US012800536B2

(12) United States Patent

Pettersson et al.

(10) Patent No.: US 12,800,536 B2

(45) Date of Patent: Nov. 17, 2026

(54) CAPACITIVE OIL SENSOR ASSEMBLY

(71) Applicant: SENSATIVE AB, Lund (SE)

(72) Inventors: Mats Pettersson, Sövde (SE); Lars Mats, Lund (SE)

(73) Assignee: Sensative AB, Lund (SE)

( * ) Notice: Subject to any disclaimer, the term of this patent is extended or adjusted under 35 U.S.C. 154(b) by 247 days.

(21) Appl. No.: 18/708,832

(22) PCT Filed: Nov. 11, 2022

(86) PCT No.: PCT/EP2022/081626

§ 371 (c)(1),
(2) Date: May 9, 2024

(87) PCT Pub. No.: WO2023/084026

PCT Pub. Date: May 19, 2023

(65) Prior Publication Data

US 2025/0003915 A1 Jan. 2, 2025

(30) Foreign Application Priority Data

Nov. 12, 2021 (EP) .................................... 21207983

(51) Int. Cl.

*G01N 27/02* (2006.01)
*G01N 27/22* (2006.01)

(Continued)

(52) U.S. Cl.

CPC ......... *G01N 27/227* (2013.01); *G01N 27/023* (2013.01); *G01N 27/028* (2013.01);

(Continued)

(58) Field of Classification Search

CPC .... G01N 27/02; G01N 27/023; G01N 27/028; G01N 27/22; G01N 27/221;

(Continued)

(56) References Cited

U.S. PATENT DOCUMENTS

2011/0217573 A1* 9/2011 Kritzer .................. G01F 23/263 429/61
2017/0146162 A1* 5/2017 Kuenstel ............... F16L 21/005

(Continued)

FOREIGN PATENT DOCUMENTS

EP 2213965 A1 8/2010
FR 2986151 A1 8/2013

(Continued)

*Primary Examiner* — Douglas X Rodriguez
*Assistant Examiner* — Kendrick X Liu
(74) *Attorney, Agent, or Firm* — Dinsmore & Shohl LLP

(57) ABSTRACT

A capacitive oil sensor assembly includes: a main body; a first conductive pad disposed on, or embedded in, the main body; and a conductive reference pad area, disposed on, or embedded in, the main body. The conductive reference pad area is connected to a ground or reference point. A gap or isolation layer separates the first conductive pad and the conductive reference pad area. The sensor assembly also includes: an electrically conductive layer; a first layer made of an oil-absorbing material, the first layer arranged between the electrically conductive layer and the main body, covering the first conductive pad and the conductive reference pad area; and a processing unit configured to measure a capacitance between the first conductive pad and the conductive reference pad area. A method of detecting oil using a capacitive oil sensor assembly is disclosed.

17 Claims, 7 Drawing Sheets

(51) Int. Cl.
*G01N 33/28* (2006.01)
*G01N 33/18* (2006.01)

(52) U.S. Cl.
CPC ......... *G01N 27/221* (2013.01); *G01N 27/223* (2013.01); *G01N 27/226* (2013.01); *G01N 27/228* (2013.01); *G01N 33/18* (2013.01); *G01N 33/28* (2013.01)

(58) Field of Classification Search
CPC .. G01N 27/223; G01N 27/226; G01N 27/227; G01N 27/228; G01N 33/26; G01N 33/28
See application file for complete search history.

(56) References Cited

U.S. PATENT DOCUMENTS

| | | | | |
|---|---|---|---|---|
| 2019/0195822 | A1* | 6/2019 | De Bruyker | G01N 27/26 |
| 2020/0173835 | A1* | 6/2020 | Zorzetto | G01F 23/268 |
| 2022/0317081 | A1* | 10/2022 | Zhe | G06N 3/04 |

FOREIGN PATENT DOCUMENTS

| | | | |
|---|---|---|---|
| JP | S5248493 | U | 4/1977 |
| JP | H09243585 | | 9/1997 |
| JP | 2011027216 | A | 2/2011 |

* cited by examiner

CAPACITIVE OIL SENSOR ASSEMBLY

CROSS-REFERENCE TO RELATED APPLICATIONS

This application is the U.S. National Stage of PCT/EP2022/081626 filed on Nov. 11, 2022, which claims priority to European Patent Application 21207983.4 filed on Nov. 12, 2021, the entire content of both are incorporated herein by reference in their entirety.

FIELD OF THE INVENTION

The present disclosure relates to capacitive oil sensor assembly for detecting the presence or addition of oil.

BACKGROUND OF THE INVENTION

An oil is a nonpolar chemical substance that is a viscous liquid at ambient temperatures and is both hydrophobic and lipophilic. Oils have a high carbon and hydrogen content and are usually flammable and surface active. Most oils are unsaturated lipids that are liquid at room temperature. Oils may be animal, vegetable, or petrochemical in origin, and may be volatile or non-volatile. Many mechanical devices use oil for lubrication purposes.

Oil sensors may be used for various reasons. They may, for example, detect an oil in a place where oil should not be, detect an oil leak from, for example, a machine or an engine, or detect outfalls from ships or industrial waste by detecting the presence of oil in or on a liquid, typically water.

Various techniques for detecting oil are described in the art. Laser nephelometers measure light scattered by particles contained in all oils. A receiving lens refocuses scattered light onto a photocell. When there is no oil, only a minimum amount of reflection occurs. When floating oil is present, reflected light intensity increases due to light scattering caused by particles in the oil. The device is an optical instrument.

A further example of an oil detector for detecting oil contamination in water is based on ultraviolet radiation. When UV radiation is sent through an oil-contaminated water sample at a peak intensity, visible radiation is emitted. The intensity of this radiation can be measured by a photocell. The intensity of this emitted radiation increases as the concentration of oil rises.

These and other conventional oil sensors are, however, associated with a number of disadvantages, including that they are relatively complex, that they cannot distinguish between oil and water or that they are not convenient to add or attach to objects or surfaces where oil is to be detected.

SUMMARY OF THE INVENTION

It is an objective of the present disclosure to provide an oil sensor assembly that overcomes some of the disadvantages of the known oil sensors. According to a first embodiment, a capacitive oil sensor assembly is provided, comprising:

- a main body;
- a first conductive pad disposed on, or embedded in, the main body;
- a conductive reference pad area, disposed on, or embedded in, the main body, wherein the conductive reference pad area is connected to a ground or reference level, and wherein a gap or isolation layer separates the first conductive pad and the conductive reference pad area; an electrically conductive layer;

- a first layer made of an oil-absorbing and water-repelling material, the first layer arranged between the electrically conductive layer and the main body, covering the first conductive pad and the conductive reference pad area; and
- a processing unit configured to measure a capacitance between the first conductive pad and the conductive reference pad area.

An example of the first embodiment is shown in FIG. 1. By sandwiching a first layer made of an oil-absorbing material between the electrically conductive layer and the main body, which comprises the first conductive pad and the conductive reference pad area (typically facing the first layer), a capacitive oil sensor assembly is achieved, which can absorb oil in the first layer (i.e. the middle layer in the "sandwich"). The absorption of oil in the first layer will change the permittivity of the first layer, which will be observed as a change in capacitance by the processing unit. The electrically conductive layer may be, for example, a metal layer. The main body, the first layer made of an oil-absorbing material and the electrically conductive layer together form a stacked assembly.

The presently disclosed oil sensor assembly can be said to build on physical and electrical principles of a capacitor. Most capacitors comprise two electrical conductors in the form of two plates, which are separated by a dielectric medium. When an electric potential difference is applied on the conductors, an electric field develops across the dielectric medium, causing a net positive charge to collect on one conductor and a net negative charge to collect on the other conductor.

In the presently disclosed capacitive oil sensor assembly, there is a first layer sandwiched between the main body comprising the first conductive pad and the conductive reference pad area, and an electrically conductive layer. The first layer is made of an oil-absorbing material. Preferably, the material of the first layer is also water-repelling. The presently disclosed oil sensor assembly is constructed such that oil can reach and be absorbed by the first layer when the oil sensor assembly is exposed to oil. The electrically conductive layer may, for example, be a base plate, such as a base plate made of metal, which can be attached to a surface in an environment in which oil may be present.

Both the first layer and the electrically conductive layer cover at least the the first conductive pad and the conductive reference pad area. In case there are further conductive pads, which is explained in further detail below, the first layer and the electrically conductive layer, generally, cover, these pads as well. In certain embodiments, the electrically conductive layer and/or the first layer may have openings for some pads.

An example of the first embodiment is shown in FIG. 1. The main body (101) has a first capacitance pad (102) and a conductive reference pad area (106) disposed on one side of the main body. In this embodiment, the first conductive pad (102) and the conductive reference area (106) are arranged in the same layer and facing the first layer (108). Preferably, the first conductive pad (102) and the conductive reference area (106) are covered by an electrically non-conductive material. The electrically non-conductive material may be any suitable material. As an example, the pads may be coated or painted with a non-conductive material. In case the capacitive oil sensor comprises additional conductive pads, these pads may also be covered by a non-conductive material. The first capacitance pad and the conductive reference pad area may be located in close proximity to each other. On top of the main body there is an oil-absorbing material. Preferably, the material is made of an oil-absorbing and water-repelling material. Such materials are commercially available. They may be based on, for example, polypropylene, or cellulose. Preferably, the material is not electrically conductive. Oil-absorbing and water-repelling materials are typically used for cleaning spills or leaks near machines or maintaining safe and clean work-spaces in, for example, industrial settings or restaurants. For the presently disclosed oil sensor assembly, the material is, preferably, arranged to cover the first capacitance pad and the conductive reference pad area, and is, preferably, used as a middle layer between the main body and an electrically conductive layer, which is placed on the first layer. When an oil is present it will be soaked by the first layer. By having the configuration of the first capacitance pad and the conductive reference pad area, the electrically conductive layer and the first layer, the electrically conductive layer is capacitively coupled to the first conductive pad and the conductive reference pad area. When the oil, which is, generally, electrically non-conductive, is introduced into the oil-absorbing first layer, the processing unit detects a change in capacitance. Capacitance refers to the ability to collect and store energy in the form of an electrical charge. The absorption of oil in the first layer will change the permittivity of the layer, which will be observed as a change in capacitance by the processing unit. The oil sensor assembly can be mounted on any suitable surface, for example by means of an adhesive, in an area where oil is to be detected. Certain embodiments of the presently disclosed oil sensor assembly can even be placed in a liquid, such as water.

Further embodiments of the presently disclosed oil sensor assembly include aspects related to further second/third/fourth conductive pads and the arrangement of the same, and array of conductive pads, further improvements and embodiments of the first layer and/or at least one water-impermeable layer configured to seal the first conductive pad or area, as well as how the processing unit may be configured to make use of these and further physical and/or mechanical configurations.

The present disclosure further relates to a method of detecting oil, comprising the steps of: providing an embodiment of the presently disclosed oil sensor assembly, measuring a capacitance between the first conductive pad and the conductive reference pad area; and determining a presence of oil based on the measured capacitance, or determining an addition of oil based on a change of the measured capacitance.

These and other aspects of the invention are set forth in the following detailed description if the invention.

BRIEF DESCRIPTION OF DRAWINGS

The invention will in the following be described with reference to the accompanying drawings, which are exemplary and not limiting to the presently disclosed capacitive oil sensor assembly.

DETAILED DESCRIPTION OF THE INVENTION

Figure 1A:
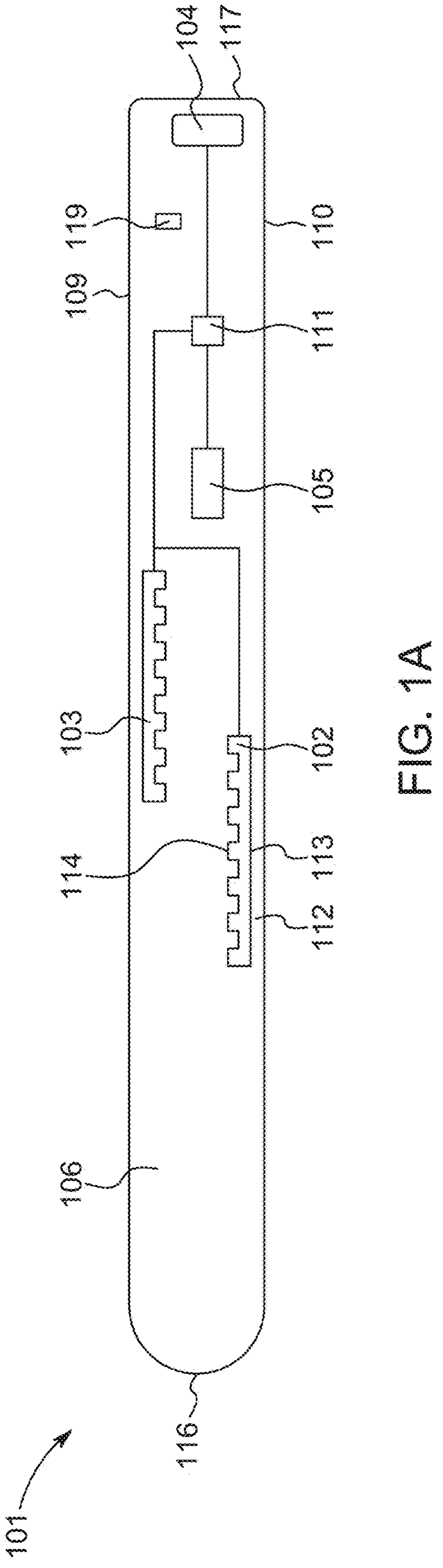
FIG. 1A-C show an exemplary embodiment of the presently disclosed capacitive oil sensor assembly.
Figure 1B:
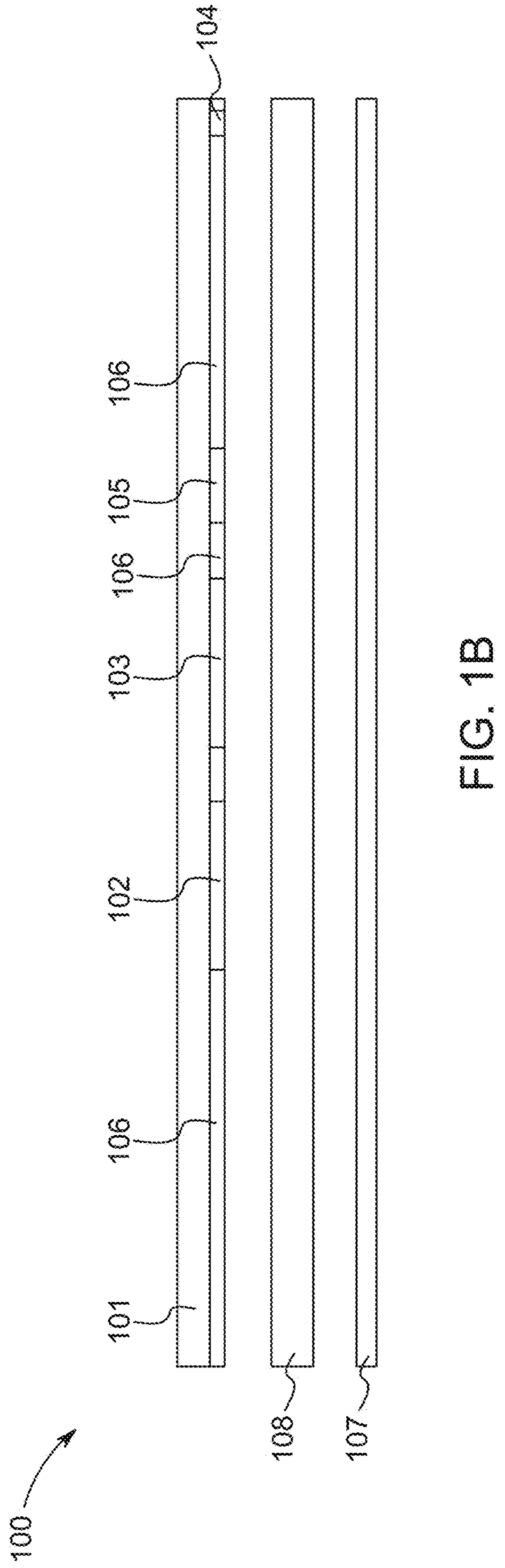
Figure 1C:
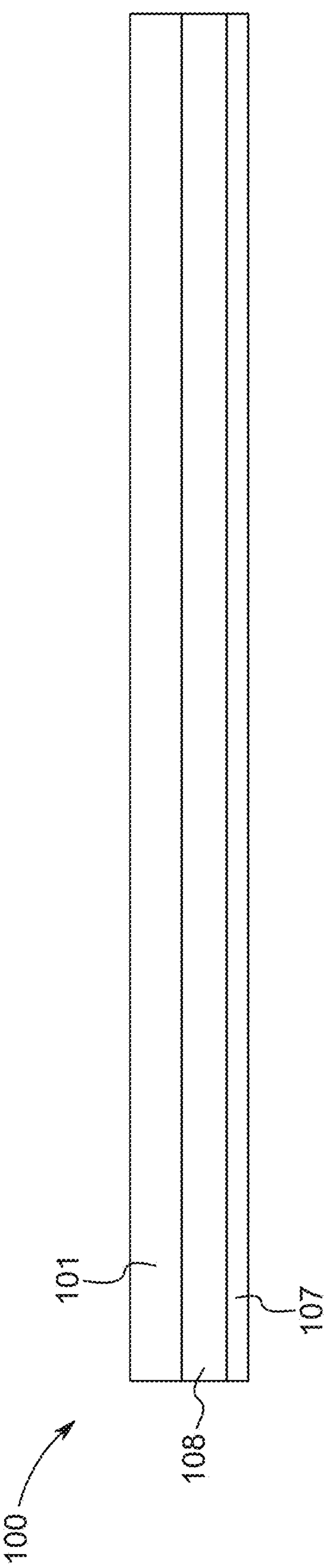

The present disclosure relates to a capacitive oil sensor assembly. The capacitive oil sensor assembly comprises a main body; a first conductive pad disposed on, or embedded in, the main body; and a conductive reference pad area, disposed on, or embedded in, the main body, wherein the conductive reference pad area is connected to a ground or reference point. Preferably, a gap or isolation layer separates the first conductive pad and the conductive reference pad area. The capacitive oil sensor assembly, preferably, further comprises a metal layer. A first layer made of an oil-absorbing material may be arranged, such as sandwiched, between the electrically conductive layer and the main body. Preferably, the first layer covers the first conductive pad and the conductive reference pad area. A processing unit may be configured to measure a capacitance between the first conductive pad and the conductive reference pad area. The processing unit may also be configured to make use of the presently disclosed arrangements in other ways. An example of the first embodiment is shown in FIG. 1. FIG. 1 shows a possibly top-view layout of the main body (101) of a capacitive oil sensor assembly. FIG. 1B shows an exploded side view of the capacitive oil sensor assembly (100) comprising the main body (101), an electrically conductive layer (107) and a first layer (108) made of an oil-absorbing material sandwiched between the electrically conductive layer (107) and the main body (101). The conductive pads (102, 103, 104, 105) are disposed on, or embedded in, a first side of the main body (101) towards the first layer (108). The conductive reference pad area is also arranged on, or embedded in, the first side of the main body (101) towards the first layer (108).

Several implementations of configurations of the processing unit are possible. In one embodiment the processing unit is configured to detect the presence of oil in the first layer as a change of capacitance between the first conductive pad and the conductive reference pad compared to air in the first layer.

Preferably, the oil-absorbing material is not only oil-absorbing but also water-repelling. Such materials are commercially available. They may be based on, for example, polypropylene, or cellulose. They may be, for example, micro polypropylene fibers. Preferably, the material is not electrically conductive. Such materials may have oil absorbent power of 10 times of its weight or more while repelling water. Accordingly, the processing unit may be configured to detect and distinguish between two different liquids, such as oil and water. If the first layer is adapted to absorb one of the liquids but not the other, the processing unit will detect a difference in capacitance for one of the liquids being soaked by the first layer and no difference, or at least a significantly lower difference, for the second liquid since it is not soaked by the first layer. Moreover, the processing unit may be configured to distinguish between two liquids, such as oil and water comprising a detergent, absorbable by the first layer, as different levels of capacitance. If water is absorbed by the material, for example by means of a detergent being present in the water, it may increase the capacitance of the material significantly since water is electrically conductive.

A number of possible arrangements and configurations are possible. These configurations are in the following paragraphs described in further detail. As would be understood by a person skilled in the art, the processing unit does not necessarily have to be physically located in the main body or a housing of the main body. The processing unit may be, for example, a micro controller. The processing unit may, alternatively, be arranged in an external unit. The external unit may be, for example, a unit connected to the main body by means of an electrical wire. The communication to the processing unit may, alternatively, be based on wireless communication. The term "capacitive oil sensor assembly" within the context of the present disclosure shall thus not be construed strictly as being implemented as one single package. The same reasoning can be applied to a battery and a wireless transmitter. All such peripheral units and components do not necessarily have to be physically arranged in the main body or the housing of the main body. Thus, alternatively, the present disclosure can be said to relate to a capacitive oil sensor system, comprising:

- a main body;
- a first conductive pad disposed on, or embedded in, the main body;
- a conductive reference pad area, disposed on, or embedded in, the main body, wherein the conductive reference pad area is connected to a ground or reference level, and wherein a gap or isolation layer separates the first conductive pad and the conductive reference pad area; an electrically conductive layer;
- a first layer made of an oil-absorbing material, the first layer arranged between the electrically conductive layer and the main body, covering the first conductive pad and the conductive reference pad area; and
- a processing unit configured to measure a capacitance between the first conductive pad and the conductive reference pad area, wherein the processing unit is part of, or located inside, the main body, or an external processing unit.

According to one embodiment, the first conductive pad and the conductive reference pad area are disposed on, or embedded in, a first side of the main body. The oil sensor assembly may have an elongate and substantially flat shape. Preferably the oil sensor assembly is thin, such as thinner than 5 mm. The length may be, for example at least 100 mm, whereas the width may be less than 20 mm. The oil sensor assembly may comprise a battery. The battery may also be then (less than 4 mm) and have a substantially elongate shape. The components may be arranged inside a housing, preferably a water-proof housing. The first side of the main body may form part of the housing.

The first conductive pad, which is disposed on, or embedded in, the main body, and the conductive reference pad area, which is also disposed on, or embedded in, the main body, may be substantially planar pads arranged on, or embedded in, the same main body. The main body may itself have a substantially flat shape, for example in the form of a printed circuit board. This means that the first conductive pad and the conductive reference pad area have a surface exposed to capture a change of capacitance in the first layer. The first layer is arranged on the first conductive pad and the conductive reference pad area to cover the first conductive pad and the conductive reference pad area. If there are further conductive pads, the first layer may cover these conductive pads as well. On top of the first layer there is an electrically conductive layer.

The first conductive pad, the conductive reference pad, and any one of further conductive pads may be arranged on, or embedded in, a substantially flat main body, such as a printed circuit board, facing away from the substantially flat main body towards the first layer and the electrically conductive layer.

The capacitive oil sensor assembly may comprise a wireless transmitter configured to communicate any measured or calculated value from the processing unit to, for example a control unit or a server. The skilled person will recognize that there are a number of options for implementing wireless communication, including for example transmitter/receiver/transceiver configured to communicate wirelessly using for example Z-Wave, ZigBee, LoRa, Bluetooth, or Bluetooth Low Energy (BLE) based communication protocols.

In one embodiment the first conductive pad and the conductive reference pad area are disposed in close proximity to each other. Preferably they are arranged in the same layer. An example is shown in FIGS. 1A and 1B. The first conductive pad (102) is arranged next to, in this particular case even surrounded by, the conductive reference area (106). In this embodiment, the first conductive pad (102) and the conductive reference area (106) are arranged in the same layer and facing the first layer (108). As would be understood by a person skilled in the art, the first conductive pad (102) and the conductive reference area (106) (or any other pad) shall not be in physical contact with each other since this will cause a short-circuit. The role of the gap or isolation layer is thus to separate the pads/reference pad from each other. It may be, for example, a thin, non-conductive, barrier. It may be an advantage that the first conductive pad and the conductive reference pad area are arranged relatively close to each other. Accordingly, the gap or isolation layer separating the first conductive pad and the conductive reference pad area may be relatively thin, such as less than 5 mm, preferably less than 3 mm, even more preferably less than 1 mm. When the first conductive pad and the conductive reference pad area are disposed in close proximity to each other, a relatively small leak may thus cover both pads, which will imply a difference in capacitance between the first conductive pad and the conductive reference pad area measurable by the processing unit. Preferably, the first conductive pad (102) and the conductive reference area (106) (and any other conductive pad) are covered by an electrically non-conductive material.

In a further embodiment, the first conductive pad has a first pad edge arranged towards and adjacent to, such as less than 5 mm, a lower edge of the main body. A part of the conductive reference pad area may be arranged in a space between the first pad edge and the lower edge of the main body. Such an embodiment is seen in FIG. 1A, wherein the first conductive pad (102) has a first pad edge (113) arranged adjacent to the lower edge (110) of the main body (101). A part of the conductive reference pad area (106) is arranged in a space (112) between the first pad edge (113) and the edge (110) of main body (101). One advantage of this embodiment is that if the oil-absorbing material is oil-absorbing and water-repelling, the processing unit (111) may see a significant difference in capacitance in case of an oil-leak since the oil will be soaked by the first layer. Water will not be soaked by the oil-absorbing and water-repelling first layer. However, since the first conductive pad (102) and the conductive reference pad area (106) are close to the edge (110) of main body (101), the processing unit may still see a significant change in capacitance if water can be present at the edge (110). Hence, in one embodiment, the first conductive pad is placed sufficiently close to an edge that the processing unit detects a first change of capacitance for a liquid not absorbed by first material and a second change of capacitance for a liquid absorbed by the first material.

According to one embodiment, the first conductive pad has a second pad edge (114) oriented towards a center of the first side of the main body, which is also illustrated in the example of FIG. 1A. One of the first pad edges (113) and second pad edge (114) may be interweaved with a corresponding pad edge of the conductive reference pad. Square-wave shaped edges is one example of such an embodiment. In FIG. 1A the second pad edge (114) and a corresponding pad edge of the conductive reference pad are substantially square-shaped. One advantage of using such shapes is that it may increase the possibility that a small leakage covers both the first conductive pad (102) and the conductive reference pad area (106). 'Interweaved' shall be construed as covering all similar shapes that provide this advantage.

The presently disclosed capacitive oil sensor assembly may further comprise a second conductive pad disposed on, or embedded in, the main body, wherein the processing unit is configured to detect a capacitance between the second conductive pad and the conductive reference pad area. Such a second conductive pad (103) is shown in FIG. 1A. The second conductive pad may be used for a number of tasks. The second conductive pad have a first pad edge arranged towards and adjacent to, such as less than 5 mm, less than 3 mm or less than 1 mm, an upper edge (109) of the main body (101). As for the first conductive pad (102), a part of the conductive reference pad area (106) may be arranged in a space between the first pad edge and the upper edge (109) of the main body (101). The second conductive pad (103) may have a second pad edge oriented towards a center of the first side of the main body. The second conductive pad (103), and any other conductive pad, may have the same arrangement of interweaved edges as the first conductive pad.

The second conductive pad may be used for increasing accuracy and ability to detect the presence of oil compared to a capacitive oil sensor assembly only having one conductive pad. For example, if the first conductive pad is arranged close to the lower edge (110) and the second conductive pad is arranged close to the upper edge (109), the processing unit may, for example, be configured to detect from which direction the oil arrives. The processing unit may be further configured to distinguish between sizes of oil leakages. If only one conductive pad detects the oil leakage, the oil leakage may be categorized as a first size oil leakage. If two or more conductive pads, with a certain minimum distance between the pads, detect an oil leakage, the processing unit may be configured to categorize the oil leakage as a second size oil leakage.

The presently disclosed capacitive oil sensor assembly may further comprise a third conductive pad disposed on, or embedded in, the main body, wherein the processing unit is further configured to detect a capacitance between the third conductive pad and the conductive reference pad area, and wherein the third conductive pad arranged at a certain minimum distance, such as at least 10 mm, from the first conductive pad. Such a second conductive pad (104) is shown in FIG. 1A. One possible purpose of such a conductive pad, which is located at a certain distance from the first conductive pad (and/or from the second conductive pad) is to determine a viscosity of a liquid absorbed by the first layer. The processing unit may be configured to measure the time it takes for oil to move from the first conductive pad to the third conductive pad (or any other conductive pad), or from the third conductive pad to the first conductive pad. The viscosity of a liquid absorbed by the first layer based on the difference in time. The third conductive pad may be arranged adjacent to a left edge (116) or a right edge (117) (as shown in FIG. 1A) of the side of the main body (101).

The presently disclosed capacitive oil sensor assembly may further comprise a fourth conductive pad disposed on, or embedded in, the main body, wherein the processing unit is further configured to detect a capacitance between the fourth conductive pad and the conductive reference pad area, and wherein the fourth conductive pad is arranged such that no external liquid can substantially impact to the capacitance of the fourth conductive pad without being absorbed by the first layer. Such a fourth conductive pad (105) is shown in FIG. 1A This typically means that the fourth conductive pad is arranged at a predefined minimum distance, such as a minimum of 5 mm, from any edge of the side of the main body. Any of the other conductive pads, for example the first conductive pad, may be arranged in this way.

Figure 2:
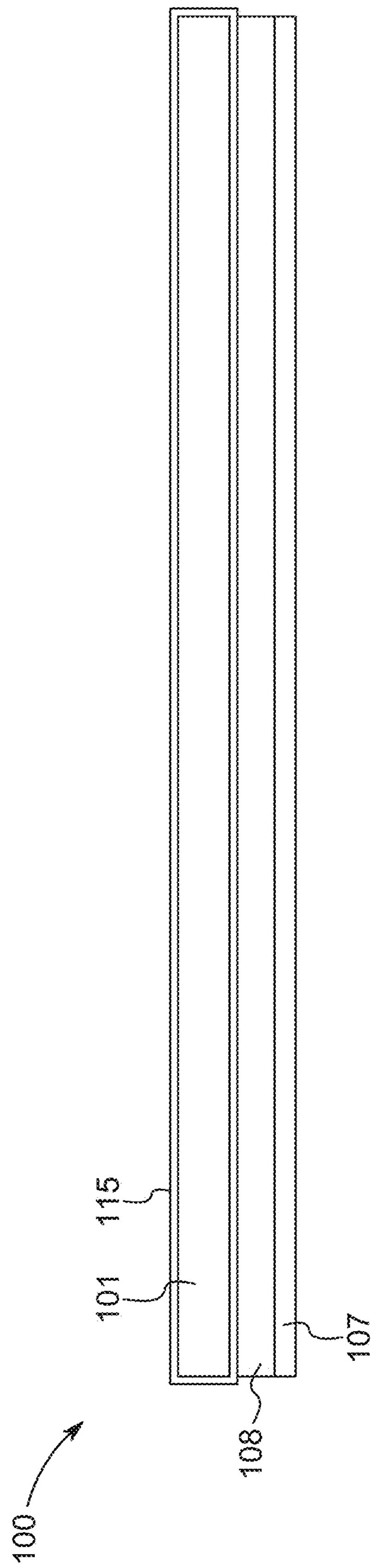
FIG. 2 shows a cross-section of a further embodiment of the presently disclosed capacitive oil sensor assembly.

In a further embodiment the presently disclosed capacitive oil sensor assembly further comprises a water-impermeable layer arranged between the conductive pads and the first layer. Preferably, the water-impermeable layer (115) encloses the main body (101) as shown in FIG. 2. The water-impermeable layer (115) may be made of any material suitable for keeping water out of the sensor. It may, for example, be a plastic. The material may not only be a water-impermeable material, but also, more generally, a liquid-impermeable layer. An electrically conductive layer (107) is arranged on top of the first layer (108). Having a water-impermeable layer arranged between the conductive pads and the first layer prevents that water short-circuits any of the conductive pads and the conductive reference pad. Even a water-repellent material may absorb water if the water comprises, for example, a detergent. An oil does not short-circuit the conductive pads and the conductive reference pad area, but another liquid may do. The first conductive pad and/or the second conductive pad and/or the third conductive pad and/or the fourth conductive pad and/or the reference pad area may, alternatively, or in combination, be coated or painted with a non-conductive material.

Figure 3:
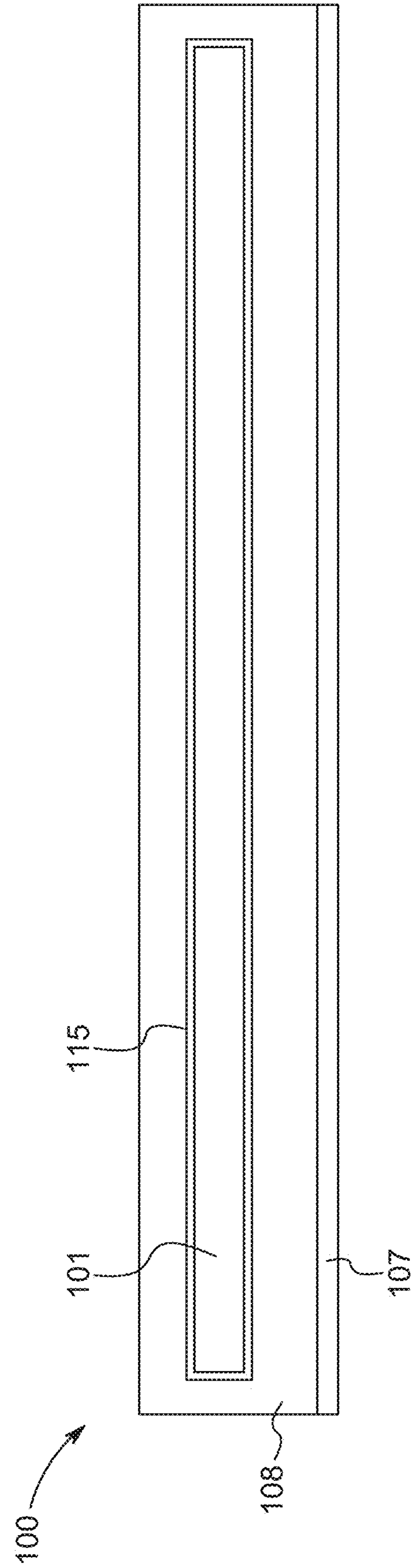
FIG. 3 shows a cross-section of a further embodiment of the presently disclosed capacitive oil sensor assembly.

In a further embodiment of the presently disclosed capacitive oil sensor assembly (100), the first layer (108) encloses the main body (101). Such an embodiment is shown in FIG. 3. An electrically conductive layer (107) is arranged on top of the first layer (108).

Figure 4:
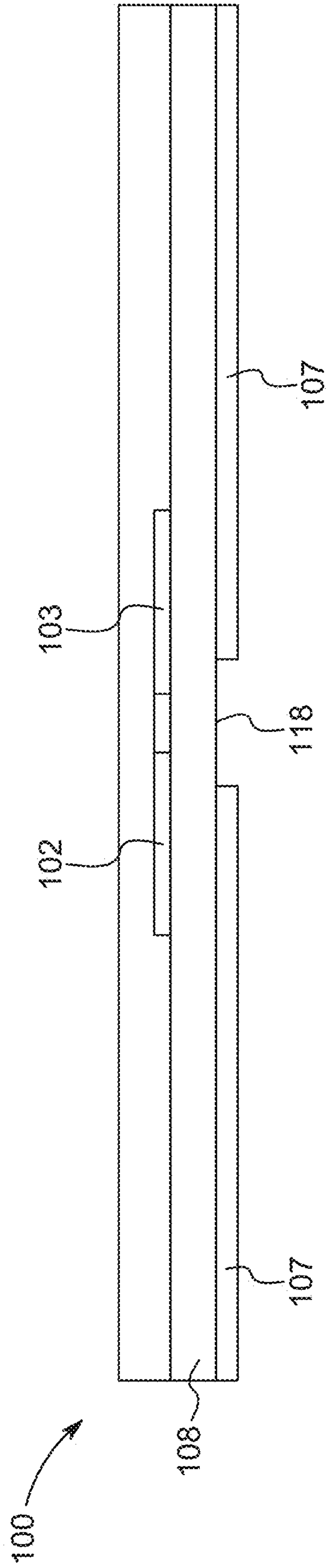
FIG. 4 shows a cross-section of an embodiment of the presently disclosed capacitive oil sensor, wherein the electrically conductive layer has an opening.

The electrically conductive layer may have at least a first opening (118) arranged at least partly at an area covering the first conductive pad (102) and/or at least a second opening arranged at least partly at an area covering the conductive reference pad area. Such an embodiment is shown in FIG. 4.

Moreover, the first layer may have at least a third opening arranged at least partly at an area covering the first conductive pad and/or at least a fourth opening arranged at least partly at an area covering the conductive reference pad area. Such opening may also be arranged at the first conductive pad and/or the fourth conductive pad. This configuration may be useful if one of the conductive pads shall be used to detect water, which would otherwise not be absorbed by the oil-absorbing and water-repelling material.

A combination of opening such that a specific conductive pad is covered neither by the first layer nor the electrically conductive layer is also possible. This configuration would typically be useful if there are several pads and one of the pads is used specifically for detecting the presence of water.

In one embodiment, the capacitive oil sensor assembly comprises at least two conductive pads. This may be, for example, a capacitive oil sensor comprising at least the first conductive pad and the second conductive pad. It may also be a capacitive oil sensor comprising at least the first conductive pad, the second conductive pad and any one of the third conductive pad and the fourth conductive pad. In such embodiments, at least one of the conductive pads may have a double-layered opening covering the conductive pad itself and a neighboring part of the reference pad area. This means that the conductive pad and the neighboring part of the reference pad area are covered neither by the first layer nor the electrically conductive layer, i.e. they are directly exposed to any liquid, which will enable it to detect, for example, water, by short-circuiting the conductive pad and the neighboring part of the reference pad area. In this embodiment at least one of the conductive pads is also covered by the first layer and the electrically conductive layer. Such embodiments can distinguish between an oil leakage and a water leakage. The capacitive oil sensor assembly in such embodiments may thus be seen as a capacitive oil and water sensor assembly.

Figure 9A:
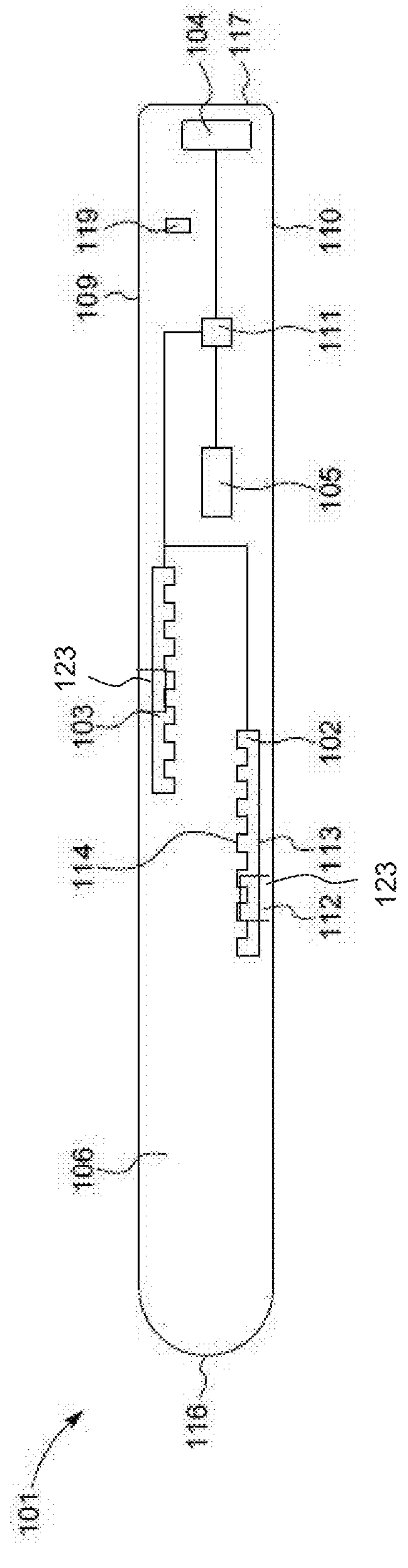
FIGS. 9A-B show an example of an embodiment of the presently disclosed capacitive oil sensor assembly having double-layered openings.
Figure 9B:
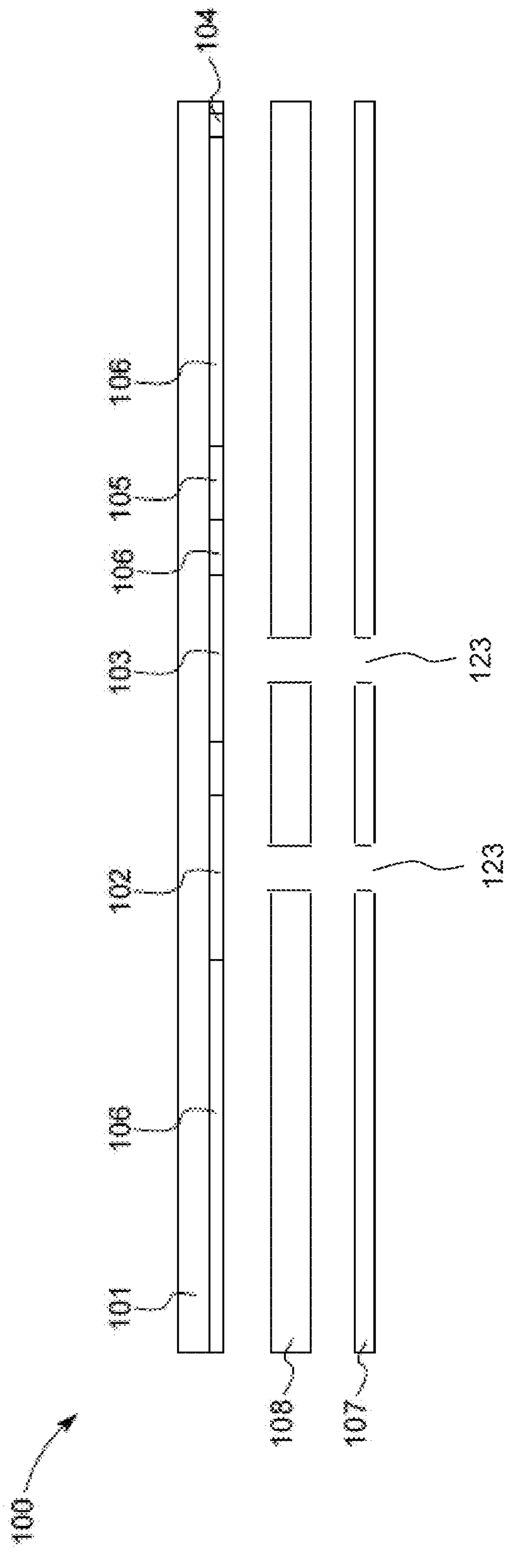

FIG. 9 shows an example of an embodiment having two double-layered openings (123). In the example one double-layered opening covers the first conductive pad (102) and a neighboring part of the reference pad area (106). Another double-layered opening covers the second conductive pad (103) and a neighboring part of the reference pad area (106). As explained the concept of direct exposure of conductive pads and neighboring part of a reference pad area is not limited to this specific example. In the example of FIG. 9 one or both of the third conductive pad and the fourth conductive pad may be used for detecting oil, whereas one or both of the first conductive pad and the second conductive pad can be used for detecting water.

The double-layered opening of at least one of the conductive pads may be supplemented by a number of openings in only the electrically conductive layers. In such an embodiment, the openings in the electrically conductive layer can be used to let oil enter into the first layer. These opening may be implemented as a number of openings spread out over the electrically conductive layer or placed adjacent to active conductive pads.

In one embodiment, the presently disclosed capacitive oil sensor assembly further comprises a second conductive pad disposed on, or embedded in, the main body and a third conductive pad disposed on, or embedded in, the main body, wherein the second conductive pad is not covered by the first layer, and wherein the third conductive pad is covered by the first layer but not covered by the electrically conductive layer. In this specific embodiment, a liquid that is not absorbed by the first layer can come in contact with the second conductive pad, which is not covered by the first layer and hence exposed to any liquid.

The processing unit may be configured to measure a difference in time of a first change in capacitance for one of the conductive pads and a second change in capacitance for another one of the conductive pads. This can be used, for example, to calculate a viscosity of an absorbed liquid. The processing unit may be configured to calculate a viscosity of a liquid absorbed by the first layer based on the difference in time. More precisely, the processing unit may be configured to determine the type of the absorbed liquid based on the calculated viscosity and permittivity at a given temperature. For this reason, the capacitive oil sensor assembly may further comprise a temperature sensor (119). The temperature sensor may be used for additional purposes. In one embodiment, processing unit is configured to categorize a detected oil as a potentially critical oil leakage, or a non-critical oil leakage based on the temperature of the detected oil.

In one embodiment, wherein at least one of the conductive pads is placed arranged at a predefined minimum distance from any edge and the capacitive oil sensor assembly comprises several conductive pads close to different edges, the processing unit may be configured to determine a magnitude of a leakage. This can be done by observing which and/or how many of the edge pads that observe the presence of oil before the pad at a predefined minimum distance from any edge observes the presence of oil.

Figure 5:
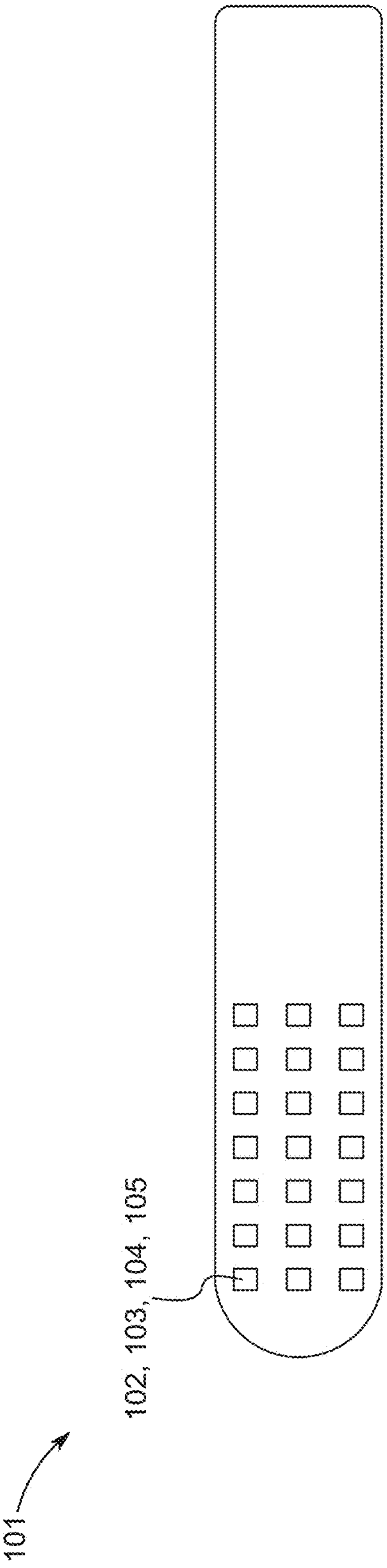
FIG. 5 shows an embodiment of the presently disclosed capacitive oil sensor, comprising an array of conductive pads.

In a further embodiment the capacitive oil sensor assembly comprises a number of conductive pads arranged in a systematic way on, or embedded in, the main body. This arrangement, in combination of special configurations of the processing unit, to which the conductive pads are connected, may extract further information. According to one embodiment the capacitive oil sensor assembly comprises an array of conductive pads disposed on, or embedded in, the main body, wherein the array of conductive pads is arranged in n rows and m columns. Such an embodiment is shown in FIG. 5. This embodiment can be used in different configuration. In one embodiment, the processing unit is configured to detect a direction and/or a speed of expansion of an absorbed oil or other liquid based on timing of changes in capacitance between individual conductive pads and the conductive reference pad area. Depending on how the array of conductive pads are arranged, the capacitive oil sensor assembly may, for example, determining the direction and/or a speed of expansion of an absorbed liquid at a relatively detailed level.

Preferably, the material of the first layer is an oil-absorbing and water-repelling material. Such materials are commercially available. A person skilled in the art would be able to get the oil-absorbing and water-repelling material and would also understand the meaning of the term. Oil-absorbents are used for, for example, cleaning leaks near heavy equipment, cleaning oil spills in industrial settings. They are also manufactured and sold for absorbing motor oil, hydraulic oil, gasoline and fuel. The presently disclosed capacitive oil sensor assembly may use the same kind of material. An example of an oil-absorbing material is provided in international application WO 2017/150740 A1.

Variants of cotton may have a waxy coating, which will allow it to absorb oil and repel water. The first layer may have a porous and/or fibrous structure. Technically, the pores of such a material may be made of, or coated with, a lipophilic material, or may comprise a lipophilic zone. The pores, or insides of the pores, may be made of, or coated with, a hydrophobic material, or may comprise a hydrophobic zone.

The first layer may be made of a relatively light material with high absorbing capacity, for example wherein the first layer comprises a cellulose or a polymer. Preferably, the first layer is made of a material that is not electrically conductive.

The present disclosure further relates to a method of detecting oil using a capacitive oil sensor assembly, comprising the steps of:

providing an oil sensor assembly comprising:

i. a first conductive pad and a conductive reference pad area disposed on, or embedded in, a main body of the sensor assembly;

ii. an electrically conductive layer;

iii. a first layer made of an oil-absorbing, and preferably water-repelling, material, the first layer arranged between the electrically conductive layer and the main body, covering the first conductive pad and the conductive reference pad area;

measuring a capacitance between the first conductive pad and the conductive reference pad area; and determining a presence of oil based on the measured capacitance and/or determining an addition of oil based on a change of the measured capacitance.

FIG. 5 shows a flow chart of an embodiment of a method of detecting oil using a capacitive oil sensor assembly (200). The method comprises the steps of: providing an oil sensor assembly comprising an oil-absorbing material (201); measuring a capacitance (202); and determining a presence of oil or an addition of oil (203).

A person skilled in the art will recognize that the presently disclosed method of detecting oil using a capacitive oil sensor assembly may use any embodiment of the presently disclosed capacitive oil sensor assembly and vice versa.

The method of detecting oil using a capacitive oil sensor assembly may, accordingly, further comprising the step of comparing a change in capacitance of:

the first conductive pad and the conductive reference pad area, and a fourth conductive pad and the conductive reference pad area.

Preferably, in this configuration, the first conductive pad has a first pad edge arranged adjacent to an edge of the main body and the fourth conductive pad is arranged at a predefined minimum distance from any edge of the side of the main body, and wherein the fourth conductive pad is arranged at a predefined minimum distance from the first conductive pad. The fact that the fourth conductive pad is arranged at a predefined minimum distance from any edge of the side of the main body makes it likely, or even certain, that the first layer has absorbed oil if a change in capacitance is observed between the fourth conductive pad and the reference pad area.

This configuration may be simplified by having only one conductive pad and the conductive reference pad area and arranging the first conductive pad at a predefined minimum distance from any edge of the side of the main body.

A number of possible further steps correspond to a number of specific embodiments of the presently disclosed capacitive oil sensor assembly. These include:

In a further embodiment the method further comprises the step of measure a difference in time of a first change in capacitance for one of the conductive pads and a second change in capacitance for another one of the conductive pads.

In a further embodiment the method further comprises the step of measuring differences in time of changes in capacitances of individual conductive pads and the conductive reference pad area for an array of conductive pads on the disposed on, or embedded in, the main body, wherein the array of conductive pads are arranged in n rows and m columns. The method may further comprise the step of determining a direction of expansion and/or a viscosity and a magnitude of a leakage of an absorbed oil or liquid.

In a further embodiment the method further comprises the step of measuring a temperature of a detected oil and determining whether the detected oil is a potentially critical oil leakage or a non-critical oil leakage based on the temperature of the detected oil.

Alternative Embodiments

The concept of implementing a capacitive oil sensor assembly comprising a first conductive pad or area; a conductive reference pad or area and a first layer made of an oil-absorbing material can be extended to alternative implementations.

The present disclosure therefore further relates to a capacitive oil sensor assembly comprising:

a first conductive pad or area;

a conductive reference pad or area, wherein the conductive reference pad or area is connected to a ground or reference point; wherein the first conductive pad or area and the conductive reference pad or area face each other;

a first layer made of an oil-absorbing material, the first layer arranged between the first conductive pad or area and the conductive reference pad or area; and a processing unit configured to detect a capacitance between the first conductive pad or area and the conductive reference pad or area.

The inventors have realized that an implementation wherein the first conductive pad or area and the conductive reference pad or area face each other, and wherein the first layer made of an oil-absorbing material is arranged between the pads, may also provide a functional capacitive oil sensor assembly.

Preferably, such a capacitive oil sensor assembly further comprises at least one water-impermeable layer configured to seal the first conductive pad or area, the conductive reference pad or area and the processing unit, and expose the first layer.

Figure 6:
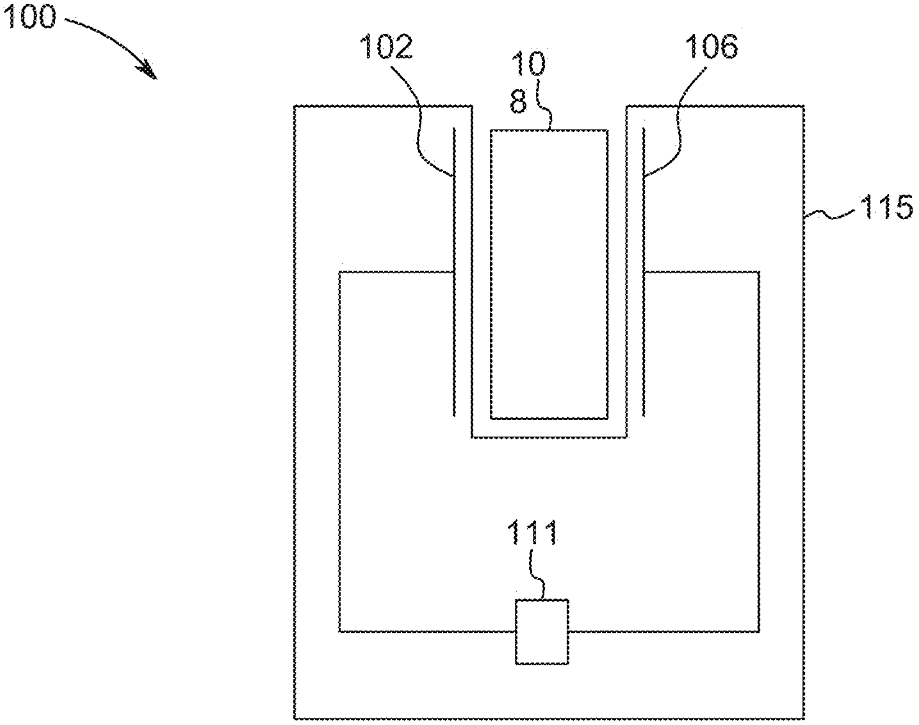
FIG. 6 shows a further embodiment of the presently disclosed capacitive oil sensor assembly, wherein the first conductive pad or area and the conductive reference pad or area face each other.

FIG. 6 shows an embodiment of such a capacitive oil sensor assembly (100). A first conductive pad or area (102) and a conductive reference pad or area (106) face each other. A first layer (108) of an oil-absorbing material is arranged between the pads (102, 106), which are connected to a processing unit (111). All components expect the first layer (108) are sealed by a water-impermeable layer (115). The first layer (108) is exposed, which means that it can absorb oil that comes in contact with the capacitive oil sensor assembly (100).

The concept can be further extended to an implementation of an inductive oil sensor assembly comprising:

a primary winding;

a secondary winding, the primary and secondary windings operatively placed side by side in an abutting relationship with each other;

a core comprising an oil-absorbing material, wherein a changing current in the primary winding causes time-varying magnetic flux in the core, which induces a current in the secondary winding; and a processing unit configured to detect a current change in the second winding to identify the absorption of an oil by the core.

The inductive oil sensor assembly may have the basic functionality of a transformer, which is a passive component that transfers electrical energy from one coil to another coil. A varying current in any one coil of the transformer produces a varying magnetic flux in the transformer's core, which induces a varying electromotive force across the other coil. The coil can have a number of shapes. When the oil-absorbing material of the core absorbs oil, it will generate change the magnetic permeability of the core.

Figure 7:
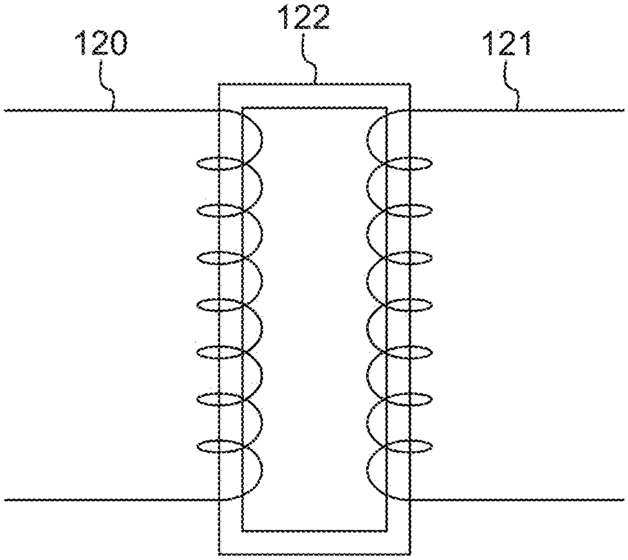
FIG. 7 shows an embodiment of an inductive oil sensor assembly.
Figure 8:
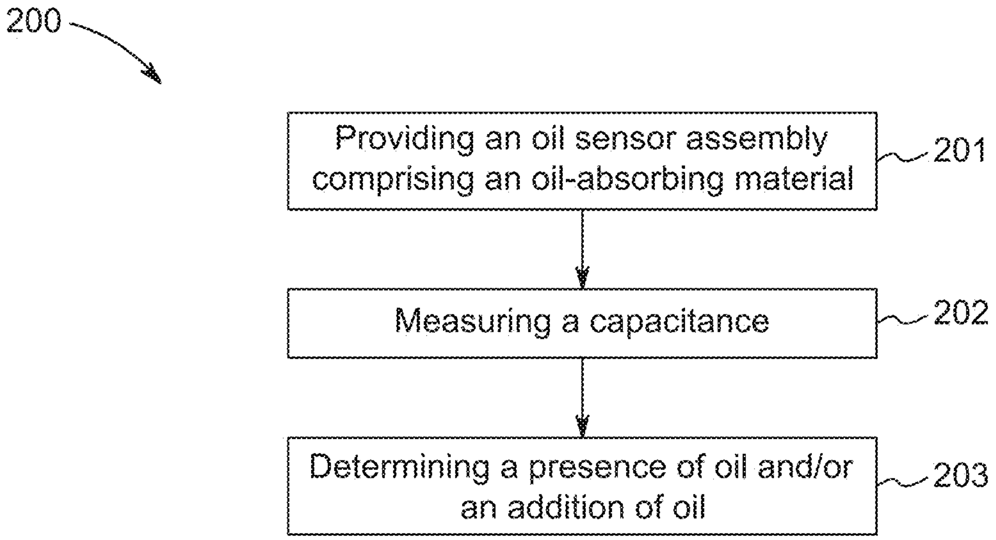
FIG. 8 shows a flow chart of an embodiment of a method of detecting oil using a capacitive oil sensor assembly.

FIG. 7 shows an embodiment of such an inductive oil sensor assembly (100). The inductive oil sensor assembly (100) comprises a primary winding (120); a secondary winding (121); and a core (122).

Preferably, such an inductive oil sensor assembly further comprises at least one water-impermeable layer configured to seal all the components except the core.

LIST OF ELEMENTS IN FIGURES

100—capacitive oil sensor assembly
101—main body
102—first conductive pad
103—second conductive pad
104—third conductive pad
105—fourth conductive pad
106—reference pad area
107—electrically conductive layer
108—first layer (made of an oil-absorbing material)
109—upper edge
110—lower edge
111—processing unit
112—space between pad edge and edge of main body
113—first pad edge
114—second pad edge
115—water-impermeable layer
116—left edge
117—right edge
118—opening
119—temperature sensor
120—primary winding
121—secondary winding
122—core
123—double-layered opening Further Details of the Invention 1. A capacitive oil sensor assembly comprising:
a main body;
a first conductive pad disposed on, or embedded in, the main body;
a conductive reference pad area, disposed on, or embedded in, the main body, wherein the conductive reference pad area is connected to a ground or reference point, and wherein a gap or isolation layer separates the first conductive pad and the conductive reference pad area;
an electrically conductive layer;
a first layer made of an oil-absorbing material, the first layer arranged between the electrically conductive layer and the main body, covering the first conductive pad and the conductive reference pad area; and a processing unit configured to measure a capacitance between the first conductive pad and the conductive reference pad area.

2. The capacitive oil sensor assembly according to item 1, wherein the processing unit is configured to detect the presence of oil in the first layer as a change of capacitance between the first conductive pad and the conductive reference pad compared to air in the first layer.

3. The capacitive oil sensor assembly according to any one of the preceding items, wherein the first conductive pad and the conductive reference pad area are disposed on, or embedded in, a first side of the main body.

4. The capacitive oil sensor assembly according to any one of the preceding items, wherein the oil-absorbing material of the first layer is an oil-absorbing and water-repelling material.

5. The capacitive oil sensor assembly according to any one of the preceding items, wherein the first conductive pad and the conductive reference area are covered by an electrically non-conductive material.

6. The capacitive oil sensor assembly according to any one of the preceding items, wherein first conductive pad has a first pad edge arranged towards and adjacent to, such as less than 5 mm, a lower edge of the main body.

7. The capacitive oil sensor assembly according to item 6, wherein a part of the conductive reference pad area is arranged in a space between the first pad edge and the lower edge of the main body.

8. The capacitive oil sensor assembly according to any one of the preceding items, wherein the conductive reference pad area and the conductive reference pad area are disposed in close proximity to each other.

9. The capacitive oil sensor assembly according to any one of the preceding items, wherein the first conductive pad is placed sufficiently close to an edge that the processing unit detects a first change of capacitance for a liquid not absorbed by first material and a second change of capacitance for a liquid absorbed by the first material.

10. The capacitive oil sensor assembly according to any one of the preceding items, wherein first conductive pad has a second pad edge oriented towards a center of the first side of the main body.

11. The capacitive oil sensor assembly according to any one of items 6-10, wherein the first pad edge and/or the second pad edge of the first conductive pad is/are interweaved, such as wherein the first pad edge and/or the second pad edge of the first conductive pad is/are square wave shaped, with a corresponding edge of the conductive reference pad.

12. The capacitive oil sensor assembly according to any one of the preceding items, further comprising a second conductive pad disposed on, or embedded in, the main body, wherein the processing unit is configured to detect a capacitance between the second conductive pad and the conductive reference pad area.

13. The capacitive oil sensor assembly according to item 12, wherein the second conductive pad has a first pad edge arranged towards and adjacent to, such as less than 5 mm, less than 3 mm or less than 1 mm, an upper edge of the main body.

14. The capacitive oil sensor assembly according to item 13, wherein a part of the conductive reference pad area is arranged in a space between the first pad edge and the upper edge of the main body.

15. The capacitive oil sensor assembly according to any one of items 12-14, wherein the second conductive pad has a second pad edge oriented towards a center of the first side of the main body.

16. The capacitive oil sensor assembly according to any one of items 12-15, wherein the first pad edge and/or the second pad edge of the second conductive pad is/are square wave shaped, and wherein a corresponding edge of the conductive reference pad area is square wave shaped.

17. The capacitive oil sensor assembly according to any one of the preceding items, further comprising a third conductive pad disposed on, or embedded in, the main body, wherein the processing unit is further configured to detect a capacitance between the third conductive pad and the conductive reference pad area, and wherein the third conductive pad arranged at a certain minimum distance, such as at least 10 mm, from the first conductive pad.

18. The capacitive oil sensor assembly according to item 17, wherein the third conductive pad is arranged adjacent to a left edge or a right edge of the side of the main body.

19. The capacitive oil sensor assembly according to any one of the preceding items, further comprising a fourth conductive pad disposed on, or embedded in, the main body, wherein the processing unit is further configured to detect a capacitance between the fourth conductive pad and the conductive reference pad area, and wherein the fourth conductive pad is arranged such that no external liquid can substantially impact to the capacitance of the third conductive pad without being absorbed by the first layer 20. The capacitive oil sensor assembly according to item 19, wherein the fourth conductive pad is arranged at a predefined minimum distance, such as a minimum of 5 mm, from any edge of the side of the main body.

21. The capacitive oil sensor assembly according to any one of items 19-20, wherein the processing unit is configured to detect two different liquids, such as oil and water, preferably wherein the first layer is adapted to absorb one of the liquids but not the other.

22. The capacitive oil sensor assembly according to any one of the preceding items, wherein the processing unit is configured to distinguish between two liquids, such as oil and water comprising a detergent, absorbable by the first layer, as different levels of capacitance.

23. The capacitive oil sensor assembly according to any one of the preceding items, wherein first conductive pad and/or the second conductive pad and/or the third conductive pad and/or the fourth conductive pad and/or the reference pad area are coated or painted with a non-conductive material.

24. The capacitive oil sensor assembly according to any one of the preceding items, wherein the electrically conductive layer has at least a first opening arranged at least partly at an area covering the first conductive pad and/or at least a second opening arranged at least partly at an area covering the conductive reference pad area.

25. The capacitive oil sensor assembly according to any one of the preceding items, further comprising a second conductive pad disposed on, or embedded in, the main body and a third conductive pad disposed on, or embedded in, the main body, wherein the second conductive pad is not covered by the first layer, and wherein the third conductive pad is covered by the first layer but not covered by the electrically conductive layer.

26. The capacitive oil sensor assembly according to any one of the preceding items, wherein the processing unit is configured to measure a difference in time of a first change in capacitance for one of the conductive pads and a second change in capacitance for another one of the conductive pads.

27. The capacitive oil sensor assembly according to item 26, wherein the processing unit is configured to calculate a viscosity of a liquid absorbed by the first layer based on the difference in time.

28. The capacitive oil sensor assembly according to item 27, wherein the processing unit is configured to determine the type of the absorbed liquid based on the calculated viscosity and permittivity at a given temperature.

29. The capacitive oil sensor assembly according to any one of the preceding items, further comprising a temperature sensor.

30. The capacitive oil sensor assembly according to item 29, wherein the processing unit is configured to categorize a detected oil as a potentially critical oil leakage or a non-critical oil leakage based on the temperature of the detected oil.

31. The capacitive oil sensor assembly according to any one of the preceding items, comprising an array of conductive pads disposed on, or embedded in, the main body, such as wherein the array of conductive pads are arranged in n rows and m columns.

32. The capacitive oil sensor assembly according to item 31, wherein the processing unit is configured to detect a direction and/or a speed of expansion of an absorbed oil or other liquid based on timing of changes in capacitance between individual conductive pads and the conductive reference pad area.

33. The capacitive oil sensor assembly according to any one of the preceding items, further comprising a water-impermeable layer arranged between the conductive pads and the first layer.

34. The capacitive oil sensor assembly according to item 33, wherein the water-impermeable layer encloses the main body.

35. The capacitive oil sensor assembly according to any one of the preceding items, wherein the first layer encloses the main body.

36. The capacitive oil sensor assembly according to any one of the preceding items, wherein the first layer has a porous and/or fibrous structure.

37. The capacitive oil sensor assembly according to item 36, wherein pores, or insides of the pores of the first layer, are made of, or coated with a lipophilic material, or comprises a lipophilic zone.

38. The capacitive oil sensor assembly according to item 37, wherein the pores, or insides of the pores, are made of, or coated with a hydrophobic material, or comprises a hydrophobic zone.

39. The capacitive oil sensor assembly according to any one of the preceding items, wherein the first layer comprises a cellulose or a polymer.

40. The capacitive oil sensor assembly according to any one of the preceding items, wherein the first layer is made of a material that is not electrically conductive.

41. A method of detecting oil using a capacitive oil sensor assembly, comprising the steps of:

- providing an oil sensor assembly comprising:
  - a first conductive pad and a conductive reference pad area disposed on, or embedded in, a main body of the sensor assembly;
  - an electrically conductive layer;
  - a first layer made of an oil-absorbing, and preferably water-repelling, material, the first layer arranged between the electrically conductive layer and the main body, covering the first conductive pad and the conductive reference pad area;
- measuring a capacitance between the first conductive pad and the conductive reference pad area; and
- determining a presence of oil based on the measured capacitance.

42. A method of detecting oil using a capacitive oil sensor assembly, comprising the steps of:

- providing an oil sensor assembly comprising:
  - a first conductive pad and a conductive reference pad area disposed on, or embedded in, a main body of the sensor assembly;
  - an electrically conductive layer;
  - a first layer made of an oil-absorbing, and preferably water-repelling, material, the first layer arranged between the electrically conductive layer and the main body, covering the first conductive pad and the conductive reference pad area;
- measuring a capacitance between the first conductive pad and the conductive reference pad area; and
- determining an addition of oil based on a change of the measured capacitance.

43. The method of detecting oil using a capacitive oil sensor assembly according to any one of items 41-42, wherein the oil sensor assembly is an oil sensor assembly according to any one of items 1-38.

44. The method of detecting oil using a capacitive oil sensor assembly according to any one of items 41-43, further comprising the step of comparing a change in capacitance of:

the first conductive pad and the conductive reference pad area, and a fourth conductive pad and the conductive reference pad area, preferably wherein the first conductive pad has a first pad edge arranged adjacent to an edge of the main body and the fourth conductive pad is arranged at a predefined minimum distance from any edge of the side of the main body, and wherein the fourth conductive pad is arranged at a predefined minimum distance from the first conductive pad.

45. The method of detecting oil using a capacitive oil sensor assembly according to any one of items 41-44, further comprising the step of measure a difference in time of a first change in capacitance for one of the conductive pads and a second change in capacitance for another one of the conductive pads.

46. The method of detecting oil using a capacitive oil sensor assembly according to any one of items 41-45, further comprising the step of measuring differences in time of changes in capacitances of individual conductive pads and the conductive reference pad area for an array of conductive pads on the disposed on, or embedded in, the main body, wherein the array of conductive pads are arranged in n rows and m columns.

47. The method of detecting oil using a capacitive oil sensor assembly according to item 46, further comprising the step of determining a direction of expansion and/or a viscosity and a magnitude of a leakage of an absorbed oil or liquid.

48. The method of detecting oil using a capacitive oil sensor assembly according to any one of items 41-47, further comprising the step of measuring a temperature of a detected oil and determining whether the detected oil is a potentially critical oil leakage or a non-critical oil leakage based on the temperature of the detected oil.

49. A capacitive oil sensor assembly comprising:

a first conductive pad or area;

a conductive reference pad or area, wherein the conductive reference pad or area is connected to a ground or reference point; wherein the first conductive pad or area and the conductive reference pad or area face each other;

a first layer made of an oil-absorbing material, the first layer arranged between the first conductive pad or area and the conductive reference pad or area; and a processing unit configured to detect a capacitance between the first conductive pad or area and the conductive reference pad or area.

50. The capacitive oil sensor assembly according to item 49, further comprising at least one water-impermeable layer configured to seal the first conductive pad or area, the conductive reference pad or area and the processing unit, and expose the first layer.

51. An inductive oil sensor assembly comprising:

a primary winding;

a secondary winding, the primary and secondary windings operatively placed side by side in an abutting relationship with each other;

a core comprising an oil-absorbing material, wherein a changing current in the primary winding causes time-varying magnetic flux in the core, which induces a current in the secondary winding; and a processing unit configured to detect a current change in the second winding to identify the absorption of an oil by the core.

The invention claimed is:

1. A capacitive oil sensor assembly comprising:

a main body;

a first pad including a first conductive pad and a conductive reference pad area, the first conductive pad disposed on, or embedded in, the main body, the conductive reference pad area, disposed on, or embedded in, the main body, wherein the conductive reference pad area is connected to a ground or reference point, and wherein a gap or isolation layer separates the first conductive pad and the conductive reference pad area;

an electrically conductive layer;

a first layer made of an oil-absorbing and water-repelling material, the first layer arranged between the electrically conductive layer and the main body, covering the first conductive pad and the conductive reference pad area;

a water-impermeable layer arranged between the first pad and the first layer, the water-impermeable layer enclosing the main body; and a processing unit configured to measure a capacitance between the first conductive pad and the conductive reference pad area.

2. The capacitive oil sensor assembly according to claim 1, wherein the processing unit is configured to detect the presence of oil in the first layer as a change of capacitance between the first conductive pad and the conductive reference pad compared to air in the first layer.

3. The capacitive oil sensor assembly according to claim 1, wherein the first conductive pad and the conductive reference area are covered by an electrically non-conductive material.

4. The capacitive oil sensor assembly according to claim 1, further comprising a second conductive pad disposed on, or embedded in, the main body, wherein the processing unit is configured to detect a capacitance between the second conductive pad and the conductive reference pad area.

5. The capacitive oil sensor assembly according to claim 4, wherein the processing unit is configured to distinguish between sizes of oil leakages by observing whether only or both of the first conductive pad and the second conductive pad detects presence of oil.

6. The capacitive oil sensor assembly according to claim 4, wherein the processing unit is configured to detect an oil expansion direction based on detection of oil at the first conductive pad and the second conductive pad.

7. The capacitive oil sensor assembly according to claim 1, wherein the main body has a substantially flat shape and wherein the first conductive pad and the conductive reference pad area face away from the substantially flat main body towards the first layer and the electrically conductive layer.

8. The capacitive oil sensor assembly according to claim 1, wherein the capacitive oil sensor assembly further comprises at least one further conductive pad, wherein the first conductive pad is used for detecting oil and wherein the at least one further conductive pad is used for detecting water.

9. The capacitive oil sensor assembly according to claim 1, wherein the processing unit is configured to distinguish between detection of oil and water.

10. The capacitive oil sensor assembly according to claim 1, further comprising a third conductive pad disposed on, or embedded in, the main body, wherein the processing unit is further configured to detect a capacitance between the third conductive pad and the conductive reference pad area, and wherein the third conductive pad arranged at a certain minimum distance, such as at least 10 mm, from the first conductive pad.

11. The capacitive oil sensor assembly according to claim 1, further comprising a fourth conductive pad disposed on, or embedded in, the main body, wherein the processing unit is further configured to detect a capacitance between the fourth conductive pad and the conductive reference pad area, and wherein the fourth conductive pad is arranged such that no external liquid can substantially impact to the capacitance of a third conductive pad without being absorbed by the first layer, wherein the processing unit is configured to detect two different liquids, such as oil and water, preferably wherein the first layer is adapted to absorb one of the liquids but not the other.

12. The capacitive oil sensor assembly according to claim 1, wherein the processing unit is configured to measure a difference in time of a first change in capacitance for the first conductive pad and a second change in capacitance for another conductive pad.

13. The capacitive oil sensor assembly according to claim 1, comprising an array of conductive pads including the first conductive pad disposed on, or embedded in, the main body, such as wherein the array of conductive pads are arranged in n rows and m columns, wherein the processing unit is configured to detect a direction and/or a speed of expansion of an absorbed oil or other liquid based on timing of changes in capacitance between individual conductive pads and the conductive reference pad area.

14. The capacitive oil sensor assembly according to claim 1, wherein the first layer encloses the main body.

15. The capacitive oil sensor assembly according to claim 1, wherein the first layer has a porous and/or fibrous structure and/or wherein pores, or insides of the pores of the first layer, are made of, or coated with a lipophilic material, or comprises a lipophilic zone.

16. An inductive oil sensor assembly comprising:

a primary winding;

a secondary winding, the primary and secondary windings operatively placed side by side in an abutting relationship with each other;

a core comprising an oil-absorbing and water-repelling material, wherein a changing current in the primary winding causes time-varying magnetic flux in the core, which induces a current in the secondary winding; and a processing unit configured to detect a current change in the second winding to identify the absorption of an oil by the core.

17. A capacitive oil sensor assembly comprising:

a main body;

a first conductive pad disposed on, or embedded in, the main body;

a conductive reference pad area, disposed on, or embedded in, the main body, wherein the conductive reference pad area is connected to a ground or reference point, and wherein a gap or isolation layer separates the first conductive pad and the conductive reference pad area;

an electrically conductive layer;

a first layer made of an oil-absorbing and water-repelling material, the first layer arranged between the electrically conductive layer and the main body, covering the first conductive pad and the conductive reference pad area; and a processing unit configured to measure a capacitance between the first conductive pad and the conductive reference pad area, and to measure a difference in time of a first change in capacitance for the first conductive pad and a second change in capacitance for another conductive pad.

* * * * *